(12) United States Patent
Rhodes et al.

(10) Patent No.: US 11,793,549 B2
(45) Date of Patent: Oct. 24, 2023

(54) CUSTOMIZED PATIENT-SPECIFIC ORTHOPAEDIC SURGICAL INSTRUMENT AND METHOD FOR PREPARING A PATIENT'S FEMUR

(71) Applicant: DEPUY SYNTHES PRODUCTS, INC., Raynham, MA (US)

(72) Inventors: James M. Rhodes, Warsaw, IN (US); Daniel D. Fritzinger, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 52 days.

(21) Appl. No.: 17/404,384

(22) Filed: Aug. 17, 2021

(65) Prior Publication Data

US 2021/0369305 A1 Dec. 2, 2021

Related U.S. Application Data

(62) Division of application No. 15/995,260, filed on Jun. 1, 2018, now Pat. No. 11,090,085.

(51) Int. Cl.
| | |
|---|---|
| *A61B 17/15* | (2006.01) |
| *A61B 17/56* | (2006.01) |
| *A61B 34/10* | (2016.01) |
| *A61B 17/17* | (2006.01) |
| *A61B 17/16* | (2006.01) |

(52) U.S. Cl.
CPC ............ *A61B 17/56* (2013.01); *A61B 17/155* (2013.01); *A61B 17/1764* (2013.01); *A61B 34/10* (2016.02); *A61B 17/1664* (2013.01); *A61B 2017/568* (2013.01); *A61B 2034/102* (2016.02); *A61B 2034/108* (2016.02)

(58) Field of Classification Search
CPC ..... A61B 17/56; A61B 17/154; A61B 17/155; A61B 17/157; A61B 17/158; A61B 17/1764
See application file for complete search history.

(56) References Cited

U.S. PATENT DOCUMENTS

| | | |
|---|---|---|
| 5,702,460 A | 12/1997 | Carls et al. |
| 2009/0087276 A1* | 4/2009 | Rose .................... A61B 17/155 409/79 |
| 2011/0307067 A1 | 12/2011 | Dees |
| 2012/0209394 A1 | 8/2012 | Bojarski et al. |
| 2013/0006251 A1 | 1/2013 | Aram et al. |

FOREIGN PATENT DOCUMENTS

| | | |
|---|---|---|
| AU | 2014262239 A1 | 12/2014 |
| WO | 2011056995 A2 | 5/2011 |

OTHER PUBLICATIONS

International Search Report, International Application No. PCT/IB2019/054148, dated Oct. 14, 2019, 6 pages.

\* cited by examiner

*Primary Examiner* — Si Ming Ku
(74) *Attorney, Agent, or Firm* — BARNES & THORNBURG LLP

(57) ABSTRACT

An orthopaedic surgical instrument includes a customized patient-specific 5-in-1 cutting block having a plurality of ribs and cutting guide slots extending between each rib. A bone-facing surface of each rib has a customized patient-specific negative contour configured to receive a portion of a corresponding positive contour of the patient's femur.

5 Claims, 12 Drawing Sheets

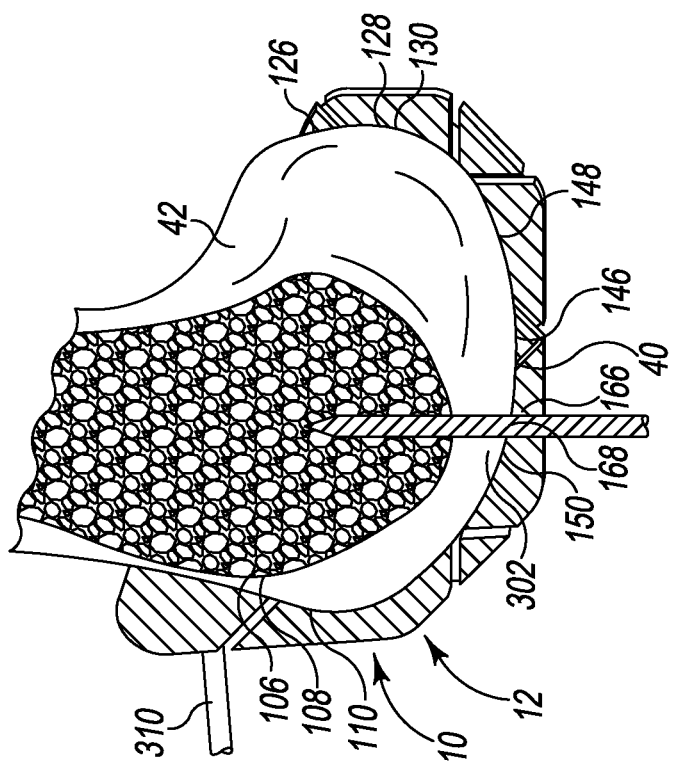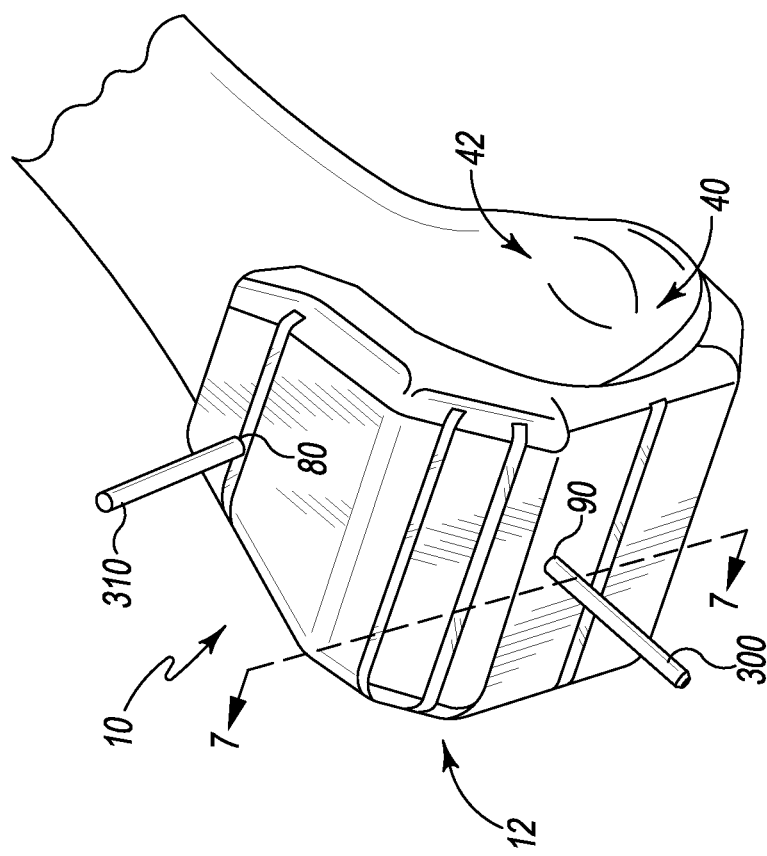

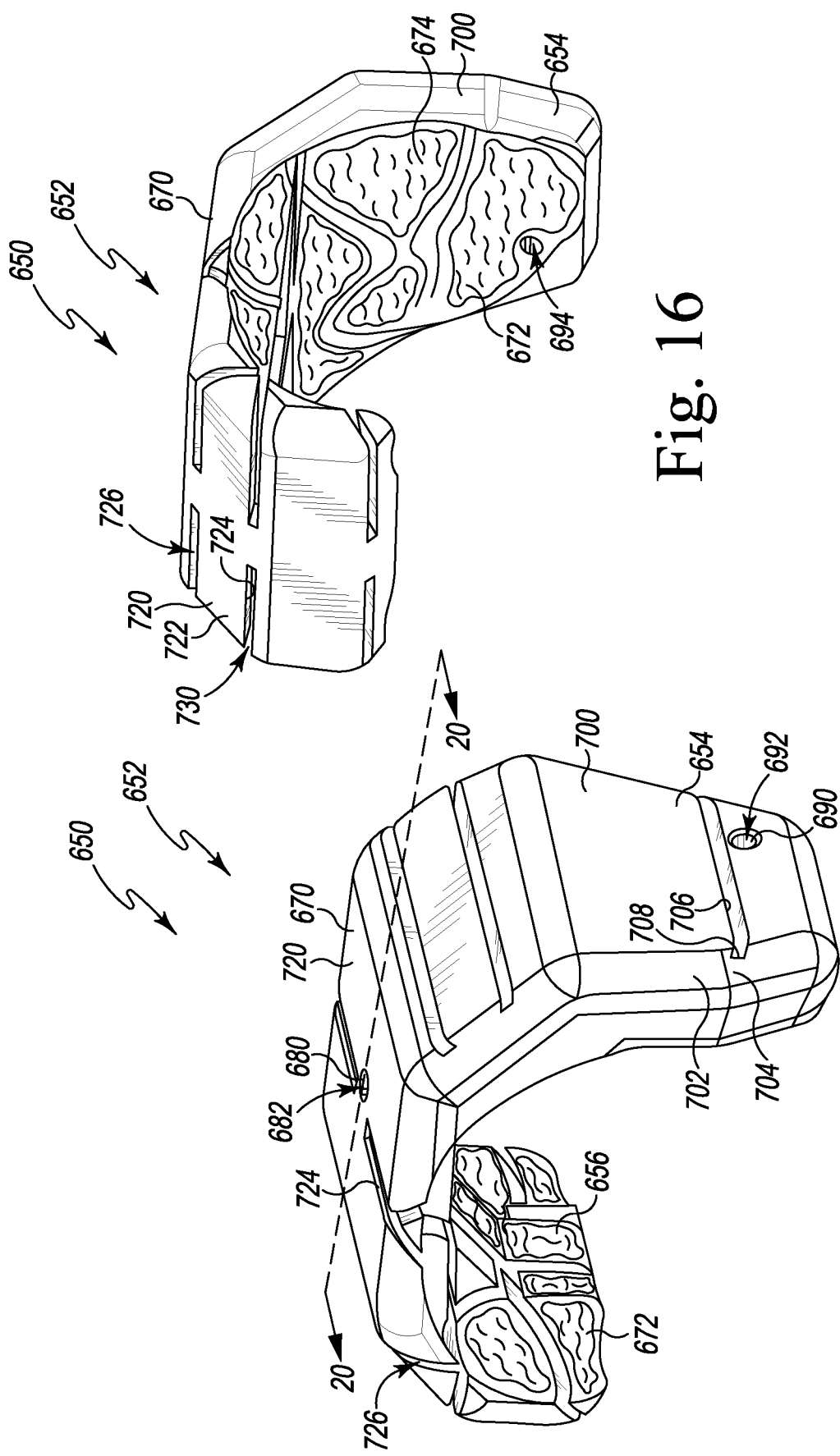

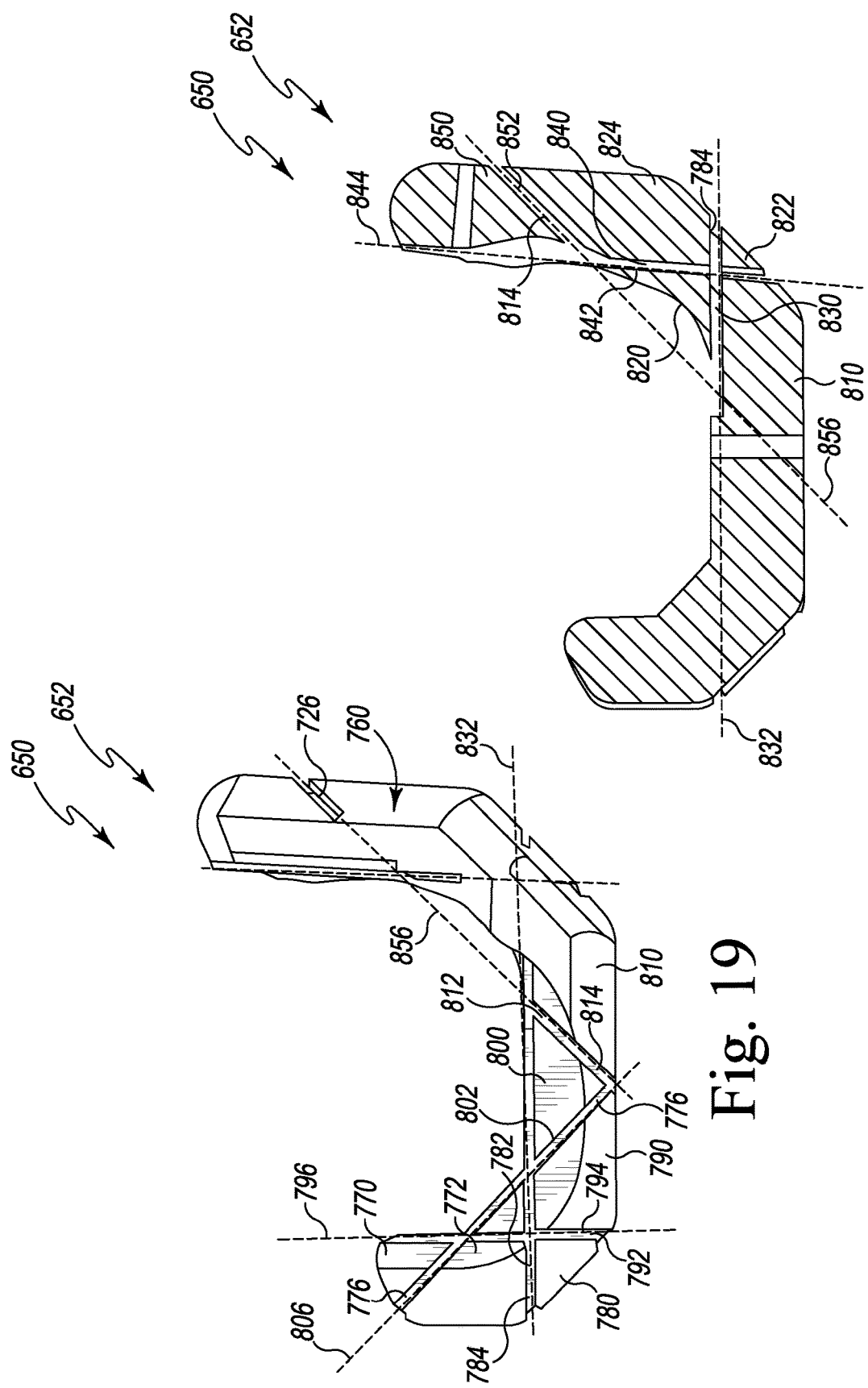

CUSTOMIZED PATIENT-SPECIFIC ORTHOPAEDIC SURGICAL INSTRUMENT AND METHOD FOR PREPARING A PATIENT'S FEMUR

This application is a divisional of, and claims priority to, U.S. patent application Ser. No. 15/995,260, now U.S. Pat. No. 11,090,085, which was filed on Jun. 1, 2018, the entirety of which is hereby incorporated by reference.

TECHNICAL FIELD

The present disclosure relates generally to orthopaedic surgical instruments and, more particularly, to customized patient-specific orthopaedic surgical instruments.

BACKGROUND

Joint arthroplasty is a well-known surgical procedure by which a diseased and/or damaged natural joint is replaced by a prosthetic joint. For example, in a total knee arthroplasty surgical procedure, a patient's natural knee joint is partially or totally replaced by a prosthetic knee joint or knee prosthesis. A typical knee prosthesis includes a tibial tray, a femoral component, and a polymer insert or bearing positioned between the tibial tray and the femoral component. In a hip replacement surgical procedure, a patient's natural acetabulum is replaced by a prosthetic cup and a patient's natural femoral head is partially or totally replaced by a prosthetic stem and femoral ball.

To facilitate the replacement of the natural joint with a prosthesis, orthopaedic surgeons use a variety of orthopaedic surgical instruments such as, for example, cutting blocks, drill guides, milling guides, and other surgical instruments. Typically, the orthopaedic surgical instruments are reusable and generic with respect to the patient such that the same orthopaedic surgical instrument may be used on a number of different patients during similar orthopaedic surgical procedures.

The orthopaedic surgical instruments may also be customized to a specific patient. Such "customized patient-specific orthopaedic surgical instruments" are single-use surgical tools for use by a surgeon in performing an orthopaedic surgical procedure that is intended, and configured, for use on a particular patient. It should be appreciated that these instruments are distinct from standard, non-patient specific orthopaedic surgical instruments that are intended for use on a variety of different patients. These customized patient-specific orthopaedic surgical instruments are distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

SUMMARY

According to one aspect of the disclosure, an orthopaedic surgical instrument includes a customized patient-specific 5-in-1 cutting block having a keel including a distal segment extending from an anterior end to a posterior end. An anterior segment extends proximally from the anterior end of the distal segment. A posterior segment extends proximally from the posterior end of the distal segment. A plurality of ribs extends medially and laterally from the distal segment, anterior segment, and the proximal segment of the keel. Each rib includes a first end coupled to the keel, a cantilevered second end, and a bone-facing surface extending from the first end to the second end of each rib. Each bone-facing surface of each rib has a customized patient-specific negative contour configured to receive a portion of a corresponding positive contour of the patient's femur. The plurality of ribs cooperate to define a plurality of cutting guides. Each cutting guide includes a slot having an open outer end defined between corresponding cantilevered second ends of adjacent ribs.

In some embodiments, the cutting guides may include a first chamfer cutting guide and a second chamfer cutting guide. Each of the first chamfer cutting guide and the second chamfer cutting guide may include medial and lateral slots. The first chamfer cutting guide may include a first slot aligned with a second slot. The second chamfer cutting guide may include a third slot aligned with a fourth slot.

In some embodiments, the cutting guides may include a distal cutting guide having medial and lateral slots. The distal cutting guide may include a first slot aligned with a second slot.

In some embodiments, the cutting guides may include an anterior cutting guide and a posterior cutting guide. Each of the anterior cutting guide and the posterior cutting guide may have medial and lateral slots.

In some embodiments, the keel may include a customized patient-specific negative contour configured to receive a portion of a corresponding positive contour of a surface defining the patient's intercondylar notch.

In some embodiments, an anterior bore may extend through the anterior segment. A distal bore may extend through the distal segment. The anterior bore and the distal bore may each be configured to receive a bone fixation pin to couple the cutting block to a distal end of the patient's femur.

According to another aspect of the disclosure, an orthopaedic surgical instrument includes a customized patient-specific 5-in-1 cutting block having an anterior flange including a bone-facing surface having a customized patient-specific negative contour configured to receive a portion of a corresponding positive contour of a patient's femur. A posterior flange includes a pair of bone-facing surfaces. Each bone facing surface of the posterior flange has a customized patient-specific negative contour configured to receive a portion of a corresponding positive contour of a patient's femoral condyle. A plurality of ribs is positioned between the anterior flange and the posterior flange. Each rib includes at least one bone-facing surface having a customized patient-specific negative contour configured to receive a portion of a corresponding positive contour of a patient's femur. A pair of beams connects adjacent ribs of the plurality of ribs. Each beam includes a bone-facing surface having a customized patient-specific negative contour configured to receive a portion of a corresponding positive contour of a patient's femur. The plurality of beams, the plurality of ribs, the anterior flange, and the posterior flange cooperate to define a plurality of captured cutting guides. Each captured cutting guide has a slot that extends from a first beam of each pair of beams to a second beam of each pair of beams.

In some embodiments, the cutting guides may include a first chamfer cutting guide and a second chamfer cutting guide. The first chamfer cutting guide may include a first slot aligned with a second slot. The second chamfer cutting guide may include a third slot aligned with a fourth slot.

In some embodiments, the cutting guides may include a distal cutting guide having a first slot aligned with a second slot.

In some embodiments, the cutting guides include an anterior cutting guide and a posterior cutting guide.

In some embodiments, an anterior bore may extend through the anterior flange. A distal bore may extend through one of the plurality of ribs. The anterior bore and the distal bore may each be configured to receive a fixation pin to couple the cutting block to a distal end of the patient's femur.

According to yet another aspect of the disclosure, an orthopaedic surgical instrument includes a customized patient-specific 5-in-1 cutting block having an anterior flange including a bone-facing surface having a customized patient-specific negative contour configured to receive a portion of a corresponding positive contour of a patient's femur. A keel includes a distal segment extending from the anterior flange to a posterior end and a posterior segment extending proximally from the posterior end of the distal segment. A plurality of ribs extends medially and laterally from the distal segment, and the proximal segment of the keel. Each rib includes a first end coupled to the keel, a cantilevered second end, and a bone-facing surface extending from the first end to the second end of each rib. Each bone-facing surface of each rib has a customized patient-specific negative contour configured to receive a portion of a corresponding positive contour of the patient's femoral condyle. The plurality of ribs cooperate to define a plurality of cutting guides. Each cutting guide includes a slot having an open outer end defined between corresponding cantilevered second ends of adjacent ribs. A plurality of captured cutting guides extends through the anterior flange.

In some embodiments, the keel may include a customized patient-specific negative contour configured to receive a portion of a corresponding positive contour of a surface defining the patient's intercondylar notch.

In some embodiments, the cutting guides include a first chamfer cutting guide and a second chamfer cutting guide. The first chamfer cutting guide may include a first slot aligned with a second slot. The second chamfer cutting guide may include a third slot aligned with a fourth slot.

In some embodiments, the cutting guides may include a distal cutting guide, an anterior cutting guide, and a posterior cutting guide.

BRIEF DESCRIPTION OF THE DRAWINGS

The detailed description particularly refers to the following figures, in which:

FIG. 6 is a perspective view of the instrument shown in FIG. 1 positioned on a distal end of a femur;

FIG. 7 is a cross-sectional view of the instrument positioned on the distal end of the femur taken along the line 7-7 in FIG. 6;

FIG. 15 is a front perspective view of yet another embodiment of a customized patient-specific orthopaedic instrument including five cutting guides for cutting a patient's femur;

FIG. 16 is another front perspective view of the instrument shown in FIG. 15;

FIG. 19 is a side elevation view of the instrument shown in FIG. 15;

FIG. 20 is a cross-sectional elevation view of the instrument taken along line 20-20 in FIG. 15;

DETAILED DESCRIPTION OF THE DRAWINGS

Figure 1:
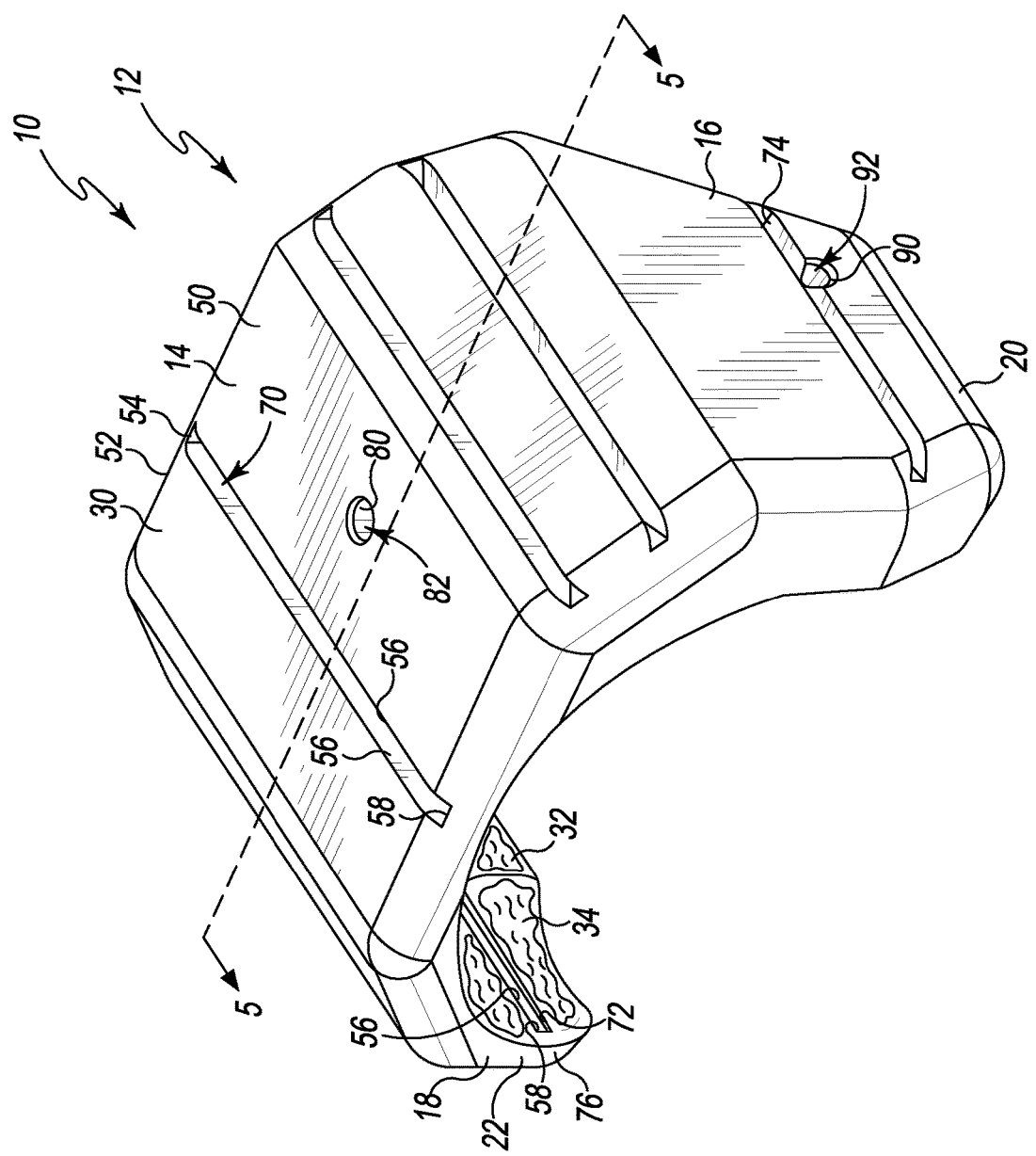
FIG. 1 is a front perspective view of an embodiment of a customized patient-specific orthopaedic instrument including five cutting guides for cutting a patient's femur.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

Terms representing anatomical references, such as anterior, posterior, medial, lateral, superior, inferior, etcetera, may be used throughout the specification in reference to the orthopaedic implants or prostheses and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

Figure 2:
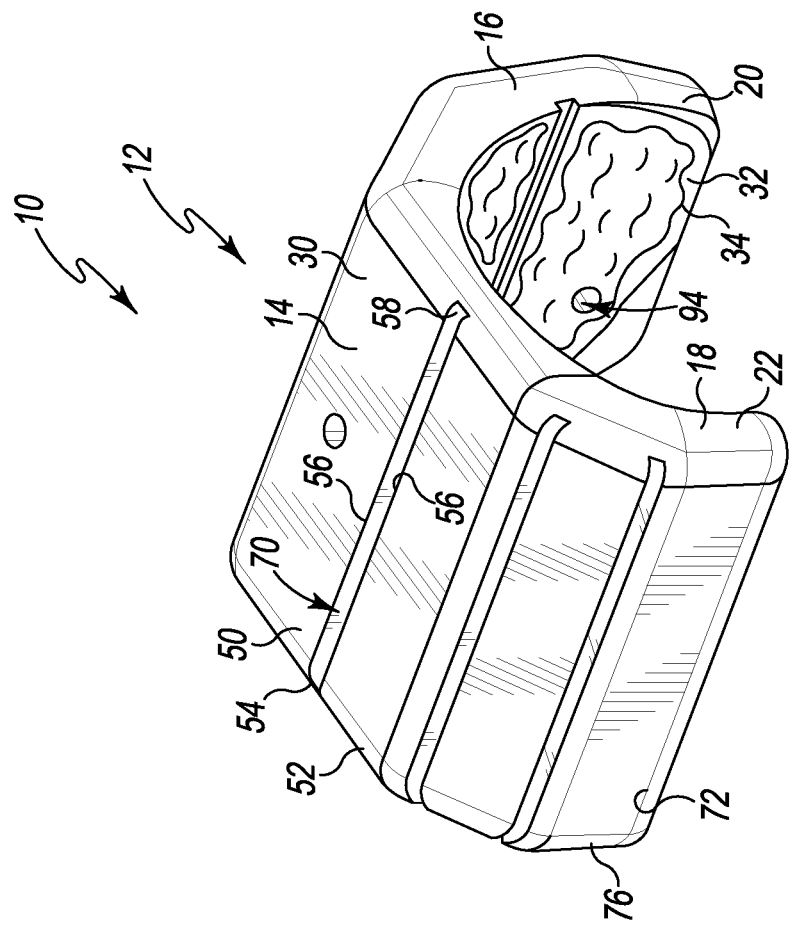
FIG. 2 is another front perspective view of the instrument shown in FIG. 1.

Referring to FIGS. 1-2, a customized patient-specific orthopaedic surgical instrument 10 is shown. As used herein, the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments (i.e., "patient-universal instruments" such as patient-universal cutting blocks) that are intended for use on a variety of different patients and were not fabricated or customized to any particular patient. Additionally, it should be appreciated that, as used herein, the term "customized patient-specific orthopaedic surgical instrument" is distinct from orthopaedic prostheses or implants, whether patient-specific or generic, which are surgically implanted in the body of the patient. Rather, an orthopaedic surgeon uses customized patient-specific orthopaedic surgical instruments to assist in the implantation of orthopaedic prostheses. Examples of "customized patient-specific orthopaedic surgical instruments" include customized patient-specific drill/pin guides, customized patient-specific tibial cutting blocks, customized patient-specific femoral cutting blocks, and customized patient-specific alignment guides. As described in greater detail below, the instrument 10 is a 5-in-1 femoral cutting block 12 configured to be coupled to the patient's femur in a unique pre-determined location and orientation.

The femoral cutting block 12 is illustratively formed by Direct Metal Laser Sintering (DMLS), also known as Selective Laser Sintering (SLS), which is a form of additive manufacturing technology. In DMLS, the femoral cutting block 12 is formed in a layer-by-layer fashion using laser sintering in which light fuses metallic powder, forming the metallic structures that define the femoral cutting block 12. It should be appreciated that other forms of additive manufacturing technology such as, for example, optical fabrication, photo-solidification, or resin printing may be used to fabricate the femoral cutting block 12. The femoral cutting block 12 is configured to be positioned on a distal end of a patient's femur (not shown) during a joint arthroplasty procedure, so that the surgeon can perform resections on the distal end of the femur. The femoral cutting block 12 enables the surgeon to perform five cuts on the distal end of the femur with a single femoral cutting block 12. Specifically, with the femoral cutting block 12, the surgeon can perform a posterior resection, an anterior resection, and a distal resection, as well as, a posterior chamfer resection and an anterior chamfer resection. The surgeon performs these resections by inserting a cutting blade through various cutting guides defined in the femoral cutting block 12 to prepare the patient's femur to receive a femoral orthopaedic prosthetic component, as described in more detail below.

The cutting block 12 includes a distal segment 14 having an anterior end 16 and a posterior end 18. An anterior flange 20 extends from the anterior end 16, and a posterior flange 22 extends from the posterior end 18. The cutting block 12 also has an outer surface 30 extends from the anterior flange 20 to the posterior flange 22. The outer surface 30 is substantially smooth. As used herein, the term "substantially" should be understood to refer to the normal tolerances created by manufacturing variation and other design criteria. As such, a "substantially smooth surface" is one that is smooth within the normal tolerances created or permitted by manufacturing variation and other design criteria. A bone-facing surface 32 of the cutting block 12 extends from the anterior flange 20 to the posterior flange 22 opposite from the outer surface 30. The bone-facing surface includes a customized patient-specific negative contour 34 that is a negative of a positive contour of a distal end 40 of a patient's femur 42 (see FIG. 6).

The distal segment 14 includes a plurality of ribs 50 that are coupled at each end 52 by beams 54. In the illustrative embodiment, each rib 50 includes a pair of planar surfaces 56, and each beam 54 includes a planar surface 58. The planar surfaces 56, 58 extend from the outer surface 30 to the bone-facing surface 32 to define a plurality of slots 70 between their planar surfaces 56 of adjacent ribs 50 and the planar surface 58 of the beam 54 connecting the adjacent ribs 50. As described in greater detail below, the slots 70 cooperate to define the cutting guides of block 12.

The posterior flange 22 of the block 12 also includes a planar surface 72, and the anterior flange 20 includes a planar surface 74. A posterior-most beam 76 couples the posterior flange 22 to an adjacent rib 50 such that a planar surface 58 of the posterior-most beam 76, the planar surface 72 of the posterior flange 22, and the planar surface 56 of the adjacent rib 50 define one of the slots 70. An anterior-most beam 79 couples the anterior flange 20 to an adjacent rib 50 such that a planar surface 58 of the anterior-most beam 78, the planar surface 74 of the anterior flange 20, and the planar surface 56 of the adjacent rib 50 define another of the slots 70.

The cutting block 12 also includes a pin guide 80, which extends from an opening 82 formed in the outer surface 30 of the distal segment 14 to an opening 84 (see FIG. 3) in the bone-facing surface 32 of the distal segment 14. The cutting block 12 includes another pin guide 90 that extends from an opening 92 formed in the outer surface 30 of the anterior flange 20 to an opening 94 (see FIG. 2) in the bone-facing surface 32 of the anterior flange 20. The pin guides 80, 90 are configured to receive bone fixation pins to retain the cutting block 12 on the distal end 40 of the patient's femur 42.

Figure 3:
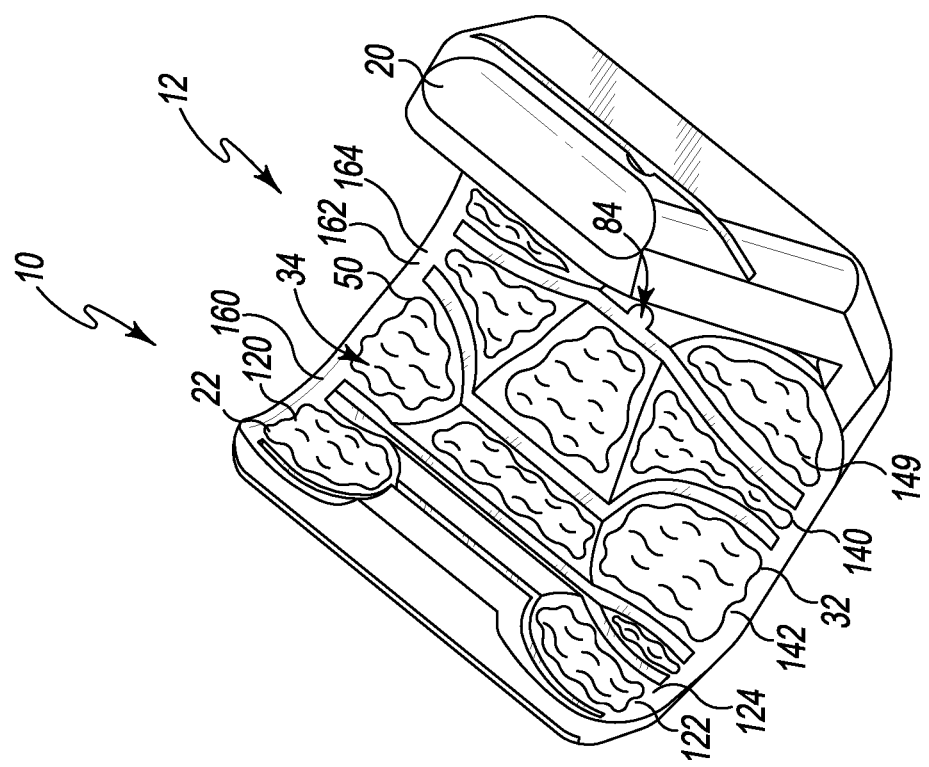
FIG. 3 is a rear perspective view of the instrument shown in FIG. 1.
Figure 4:
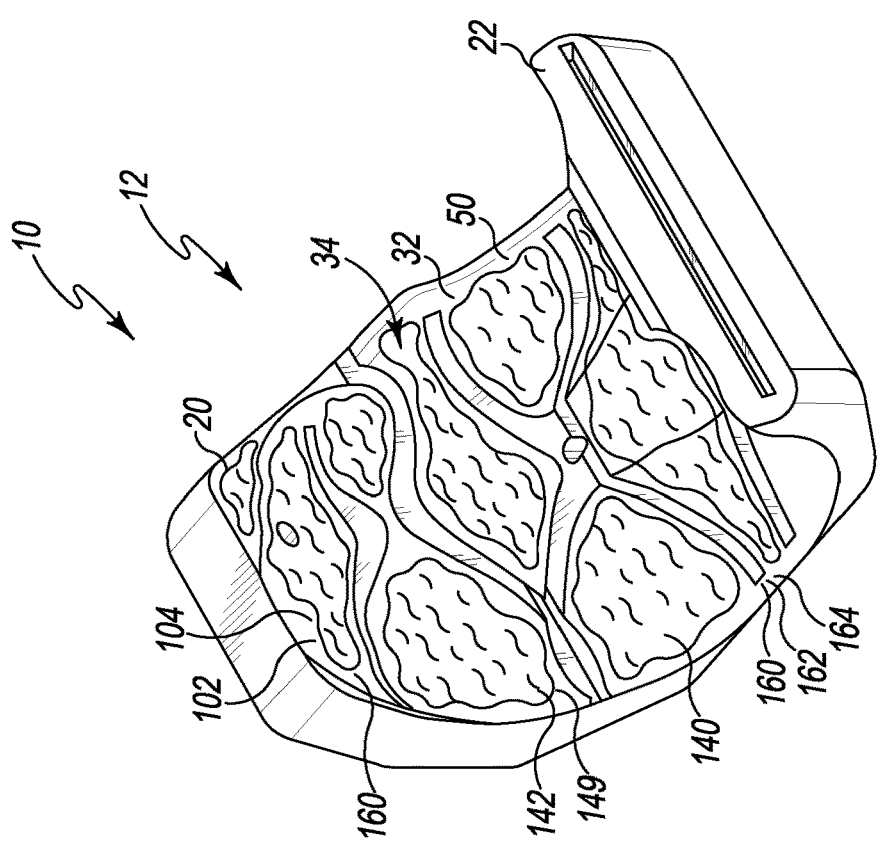
FIG. 4 is another rear perspective view of the instrument shown in FIG. 1.

Referring now to FIGS. 3-4, the negative contour 34 of the bone-facing surface 32 is formed by a number of negative contours defined in the flanges 20, 22, the ribs 50, and the beams 54. Specifically, in the illustrative embodiment, the anterior flange 20 of the cutting block 12 includes a negative contour 100 that forms a portion of the bone-facing surface 32. The contour 100 has a unique set of ridges 102 and depressions 104 that are shaped to engage a corresponding unique set of depressions 106 and ridges 108 of an anterior surface 110 of the patient's femur 42 (see FIG. 7). The posterior flange 22 also includes a negative contour 120 that forms a portion of the bone-facing surface 32. The contour 120 has a unique set of ridges 122 and depressions 124 that are shaped to engage a corresponding unique set of depressions 126 and ridges 128 of a posterior surface 130 of the patient's femur 42 (see FIG. 7). The ribs 50 of the block 12 also cooperate to define a negative contour 140 that forms a portion of the bone-facing surface 32. The contour 140 has a unique set of ridges 142 and depressions 144 that are shaped to engage a corresponding unique set of depressions 146 and ridges 148 of the condyles 150 of the patient's femur 42 (see FIG. 7). The beams 54 cooperate to define a negative contour 160 that forms a portion of the bone-facing surface 32. The contour 160 has a unique set of ridges 162 and depressions 164 that are shaped to engage a corresponding unique set of depressions 166 and ridges 168 of the distal end 40 of the patient's femur 42 (see FIG. 7).

The negative contour 34 formed by the contours 100, 120, 140, and 160 is patient-specific and matches a corresponding contour (or contours) of the distal end 40 of the patient's femur 42. In that way, the bone-facing surface 32 enables the cutting block 12 to be positioned on the distal end 40 of the patient's femur 42 in a unique, pre-planned position so that the cutting block 12 does not have to be adjusted on the distal end 40 of the femur 42 during use. In the illustrative embodiment, the cutting block 12 does not require augments to offset the cutting block 12 relative to the distal end 40 of the femur 42. As such, the cutting block 12 is positioned directly on the distal end 40 of the femur 42 and secured to the femur 42. As described below, five resections can then be performed with a single cutting block 12 without requiring any repositioning during the surgical procedure.

Figure 5:
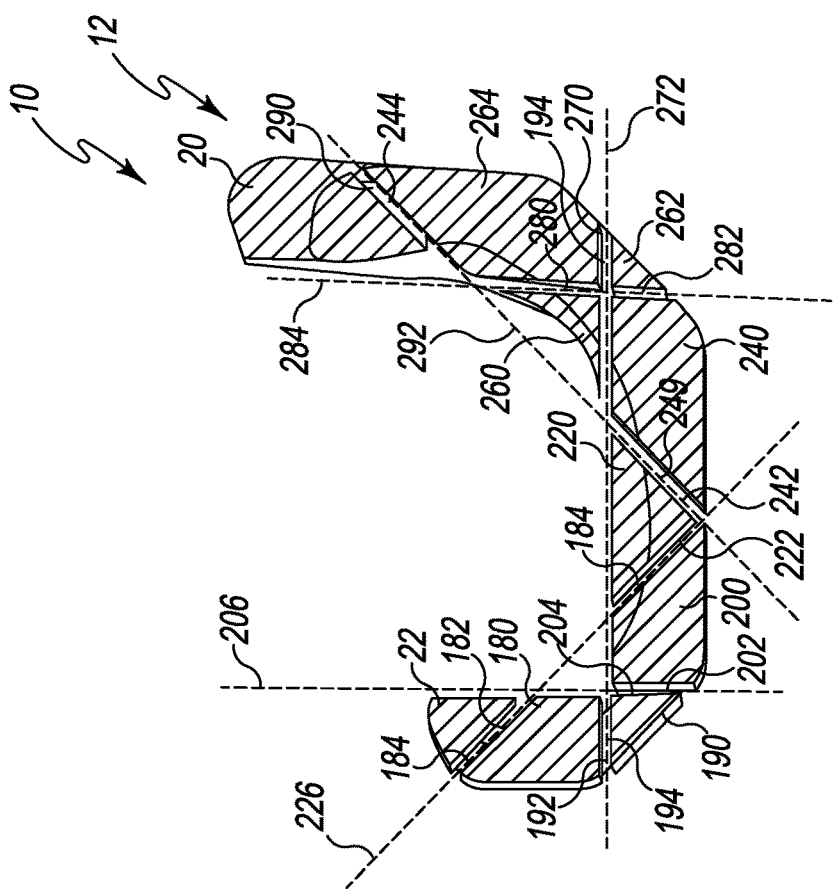
FIG. 5 is a cross-sectional elevation view taken along line 5-5 in FIG. 1.

Referring now to FIG. 5, the cutting block 12 includes a posterior chamfer cutting guide 184, a posterior cutting guide 204, a anterior chamfer cutting guide 244, a distal cutting guide 194, and an anterior cutting guide 282. To define the posterior chamfer cutting guide 184, the posterior flange 22 and a rib 180 define a slot 182 between their planar surfaces 72 and 56. A rib 200 and a rib 220 of the distal segment 14 define a slot 222 between their planar surfaces 56. The slot 222 is aligned with the slot 182 to define the captured posterior chamfer cutting guide 184. The captured posterior chamfer cutting guide 184 is configured to receive a cutting tool, and it defines a posterior chamfer resection guide plane 226 for the cutting tool that extends through the distal end 40 of the patient's femur 42.

A rib 190 and the rib 200 cooperate to define a slot 202 between their planar surfaces 56. The slot 202 defines the captured posterior cutting guide 204, which is configured to receive a cutting tool and defines a posterior resection guide plane 206 extending through the patient's femur 42.

To define the anterior chamfer cutting guide 244, the block 12 includes a rib 220 and a rib 240 that define another slot 242 between their planar surfaces 56. Another rib 264 and the anterior flange 20 define a slot 290 between their planar surfaces 74 and 56. The slot 290 is aligned with the slot 242 to define the captured anterior chamfer cutting guide 244, which is configured to receive a cutting tool to perform and defines an anterior chamfer resection guide plane 292 extending through the distal end 40 of the patient's femur 42.

To define the distal cutting guide 194, the ribs 180, 190 define a slot 192 between their planar surfaces 56. The ribs 240, 260, 262, and 264 all cooperate to define a slot 270 between their planar surfaces 56. The slot 270 is aligned with the slot 192 to define the captured distal cutting guide 194, which is configured to receive a cutting tool to perform a distal resection guide plane 272 extending through the distal end 40 of the patient's femur 42.

The anterior cutting guide 282 includes a slot 280 that is defined between their planar surfaces 56 of the ribs 240, 260, 262, and 264 the anterior cutting guide 28 is configured to receive a cutting tool and defines an anterior resection guide plane 284 extending through the distal end 40 of the anterior surface 110 of the patient's femur 42.

Referring now to FIG. 6, the pin guide 90 is sized to receive a pin 300 that secures the cutting block 12 to the distal end 40 of the patient's femur 42. The pin 300 is positioned in the patient's intercondylar notch 302, as illustrated in FIG. 7, and is secured to a surface 304 that defines the intercondylar notch 302. The pin guide 80 is sized to receive another pin 310 that secures the anterior flange 20 to the anterior surface 110 of the patient's femur 42. Because the pins 300, 310 are located in regions of the bone that are not resected during surgery, the pins 300, 310 may remain in place while the surgeon performs the resections. In some embodiments, the surgeon may remove the pin 300 when making some of the cuts so that the surgeon does not have to resect around the pin 300. In such an embodiment, the pin 310 in cooperation with the bone-facing surface 32 holds the cutting block 12 is place on the patient's femur 42.

Figure 8:
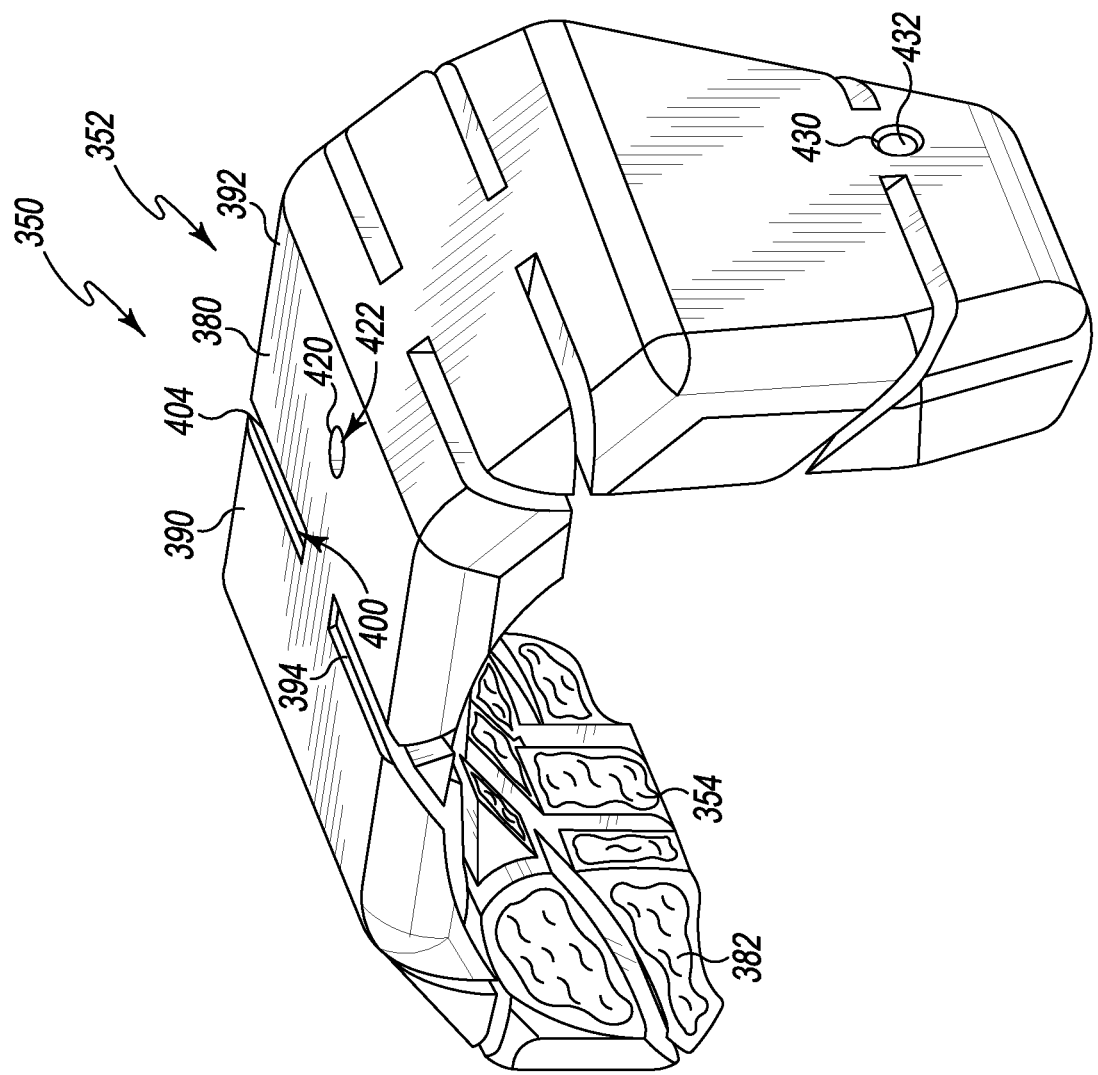
FIG. 8 is a front perspective view of another embodiment of a customized patient-specific orthopaedic instrument including five cutting guides for cutting a patient's femur.
Figure 10:
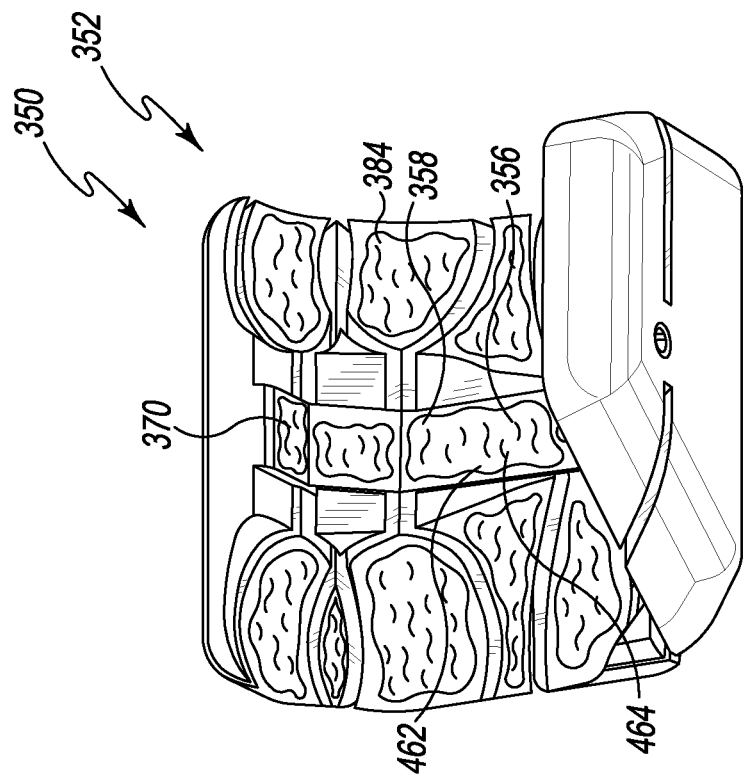
FIG. 10 is a rear perspective view of the instrument shown in FIG. 8.
Figure 9:
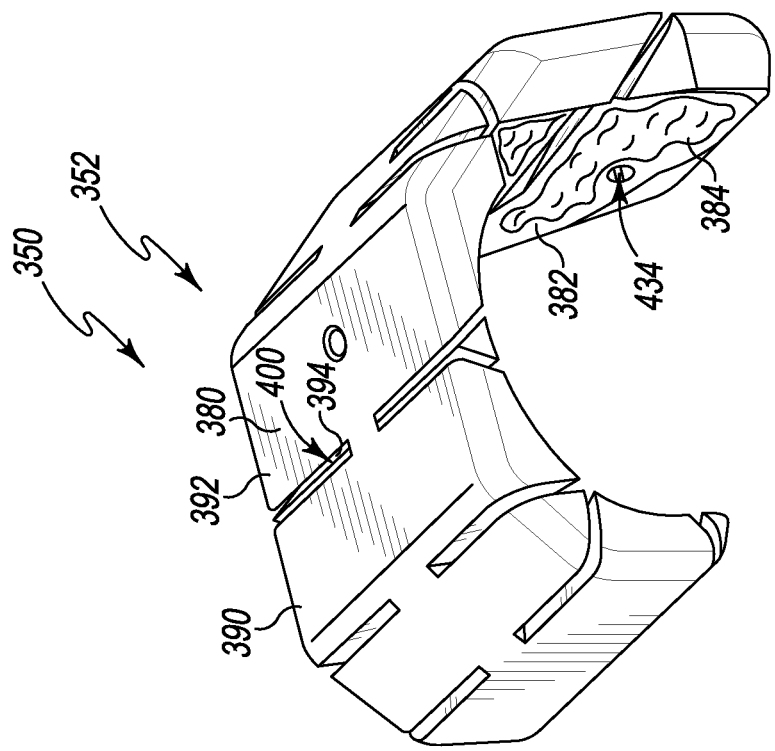
FIG. 9 is another front perspective view of the instrument shown in FIG. 8.

Referring now to FIGS. 8-9 another customized patient-specific orthopaedic surgical instrument 350 includes a 5-in-1 cutting block 352. Similar to the femoral cutting block 12, the cutting block 352 also includes a bone-facing surface 382 and an outer surface 380 that is positioned opposite the bone-facing surface 382. The bone-facing surface 382 includes a customized patient-specific contour 384 that matches and is a negative of a positive contour of a distal end 40 of a patient's femur 42 (see FIG. 13).

The cutting block 352 includes a keel 354 that extends along the mid-line of the block 352. The keel 354 includes a distal segment 356 extending between a posterior end 358 and an anterior end 360. A posterior segment 370 of the keel 354 extends from the posterior end 358 of the distal segment 356, and an anterior segment 372 of the keel 354 extends from the anterior end 360 of the distal segment 356. A plurality of medial and lateral ribs 390 extend from the keel 354 to cantilevered ends 392. Each rib 390 includes a pair of planar surfaces 394 extending from the outer surface 380 to the bone-facing surface 382. A plurality of medial and lateral slots 400 are defined by the planar surfaces 394 of adjacent ribs 390 and a planar surface 402 of the keel 354 that extends between the outer surface 380 and the bone-facing surface 382. The slots 400 include open ends 404 positioned between the cantilevered ends 392 of the ribs 390. As described in greater detail below, the slots 400 cooperate to define the five cutting guides of the block 352.

Figure 11:
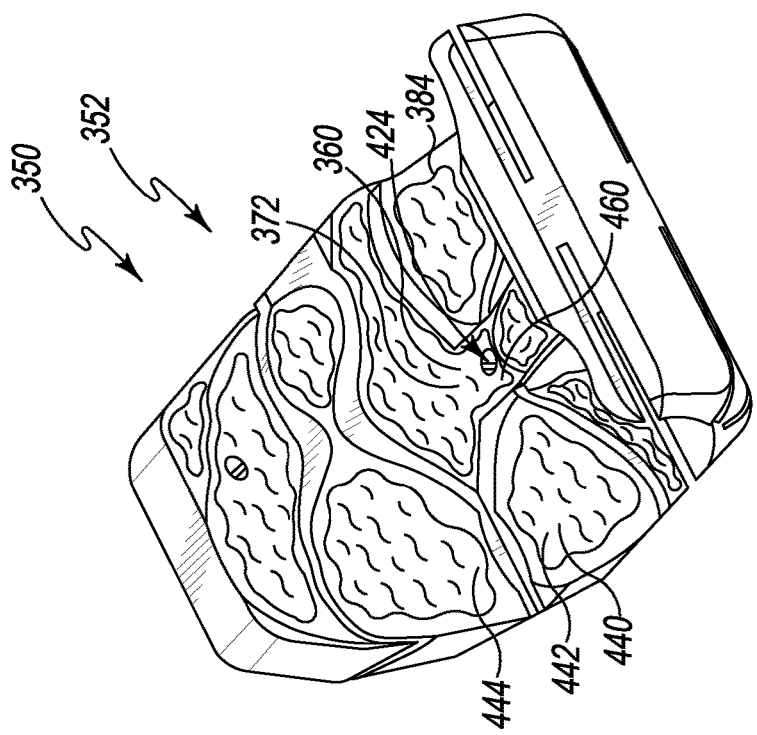
FIG. 11 is another rear perspective view of the instrument shown in FIG. 8.

The block 352 also includes a pair of pin guides 420, 430 sized to receive bone fixation pins to secure the block 352 to the patient's femur. In the illustrative embodiment, each of the pin guides 420, 430 extends through the keel 354. As shown in FIG. 11, the pin guide 420 extends from an opening 422 formed in the outer surface 380 of the distal segment 356 to an opening 424 in the bone-facing surface 382 of the distal segment 356. As shown in FIG. 9, the pin guide 430 extends from an opening 432 formed in the outer surface 380 of the anterior segment 372 to an opening 434 in the bone-facing surface 382 of the anterior segment 372.

The customized patient-specific contour 384 is formed by a number of negative contours 440, 460 defined in the ribs 390 and the keel 354, respectively. Each contour 440 has a unique set of ridges 442 and depressions 444 that are shaped to engage a corresponding unique set of depressions 166 and ridges 168 of the distal end 40 of the patient's femur 42 (see FIG. 14). The contour 460 of the keel 354 has a unique set of ridges 462 and depressions 464 that are shaped to engage a corresponding unique set of depressions 166 and ridges 168 of the distal end 40 of the patient's femur 42

Figure 12:
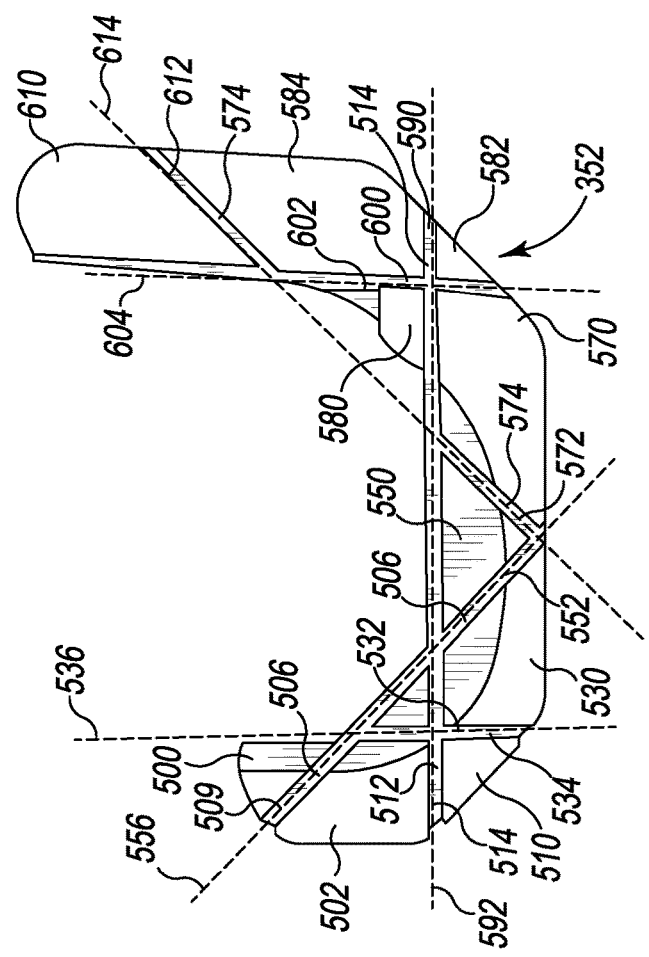
FIG. 12 is a side elevation view of the instrument shown in FIG. 8.

Referring now to FIG. 12, the various medial slots 400 of the cutting block 352 are shown on a medial side 470 of the cutting block 352. It should be noted that in the illustrative embodiment the lateral side of the cutting block 352 includes the same slots described herein with respect to the medial side 470. For example, when a distal cutting slot is referenced, it should be appreciated that the lateral side of the cutting block 352 also includes a distal lateral cutting slot that corresponds to the distal cutting slot on the medial side 470 of the cutting block 352. In that way, the medial and lateral cutting slots cooperate to define a posterior chamfer cutting guide 506, a posterior cutting guide 534, a distal cutting guide 514, an anterior chamfer cutting guide 574, and an anterior cutting guide 602 of the block 352.

To define the posterior chamfer cutting guide 506, the cutting block 352 includes a rib 500 and a rib 502 that define a slot 504 between their planar surfaces 394. Another rib 530 and a rib 550 define another slot 552 between their planar surfaces 394. The slot 552 is aligned with the slot 504 to define the medial side of the posterior chamfer cutting guide 506, which is configured to receive a cutting tool and defines a posterior chamfer resection guide plane 556 extending through the distal end 40 of the patient's femur 42. As described above, another pair of slots on the lateral side of the block 352 cooperate to define the lateral side of the posterior chamfer cutting guide 506.

The rib 530 and another rib 510 cooperate to define a slot 532 between their planar surfaces 394. The slot 532 defines the medial side of the open posterior cutting guide 534. As described above, another pair of slots on the lateral side of the block 352 cooperate to define the lateral side of the posterior cutting guide 534. The posterior cutting guide 534 is configured to receive a cutting tool and defines a posterior resection guide plane 536 extending through the patient's femur 42.

The rib 502 of the cutting block 12 and the rib 510 define a slot 512 between their planar surfaces 394. The cutting block 12 also includes ribs 570, 580, 582, and 584, which cooperate to define a slot 590 between their planar surfaces 394. The slot 590 is aligned with the slot 512 to define the medial side of the distal cutting guide 514. As described above, another pair of slots on the lateral side of the block 352 cooperate to define the lateral side of the distal cutting guide 514. The distal cutting guide 514 is configured to receive a cutting tool and defines a distal resection guide plane 592 extending through the distal end 40 of the patient's femur 42.

The ribs 550, 570 define another slot 572 between their planar surfaces 394. The rib 584 and a rib 610 define a slot 612 between their planar surfaces 394. The slot 612 is aligned with the slot 572 to define the medial side of the anterior chamfer cutting guide 574. As described above, another pair of slots on the lateral side of the block 352 cooperate to define the lateral side of the anterior chamfer cutting guide 574. The anterior chamfer cutting guide 574 is configured to receive a cutting tool and defines an anterior chamfer resection guide plane 614 extending through the distal end 40 of the patient's femur 42.

The ribs 570, 580, 582, and 584 also cooperate to define a slot 600 between their planar surfaces 394. The slot 600 defines a medial side of the open anterior cutting guide 602 that is configured to receive a cutting tool and defines an anterior resection guide plane 604 extending through the patient's femur 42.

Figure 14:
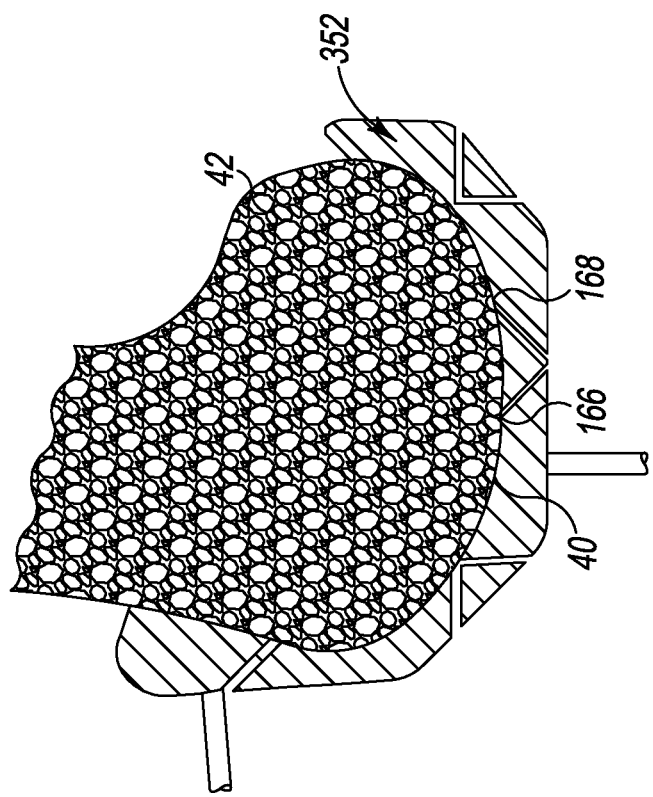
FIG. 14 is a cross-sectional view of the instrument positioned on the distal end of the femur taken along the line 14-14 in FIG. 13.
Figure 13:
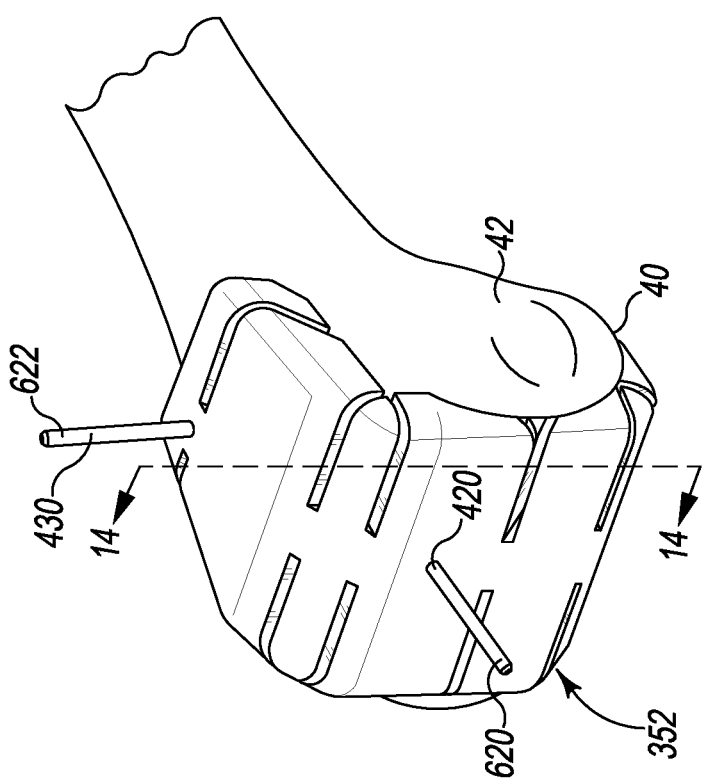
FIG. 13 is a perspective view of the instrument shown in FIG. 8 positioned on a distal end of a femur.

Referring now to FIG. 13, the pin guide 420 receives a bone fixation pin 620 that secures the cutting block 352 to the distal end 40 of the patient's femur 42. The pin 620 is positioned in the patient's intercondylar notch 302, as illustrated in FIG. 14, and is secured to a surface 304 that defines the intercondylar notch 302. The other pin guide 430 is configured to receive a fixation pin 622 that secures the anterior segment 372 to the anterior surface 110 of the patient's femur 42. The surgeon can resect around the pins 620, 622 because the pins engage portions of the bone that are not resected during a surgical procedure. In some embodiments, the surgeon may remove the pin 620 when making some of the cuts so that the surgeon does not have to resect around the pin 620. In such an embodiment, the pin 622 in cooperation with the bone-facing surface 382 holds the cutting block 352 in place on the patient's femur 42.

Referring now to FIGS. 15-16, another customized patient-specific orthopaedic surgical instrument 650 includes a 5-in-1 cutting block 652. Similar to the other cutting blocks 12 and 352, the cutting block 562 includes a bone-facing surface 672 and an outer surface 670 that is positioned opposite the bone-facing surface 672. The bone-facing surface 672 includes a customized-patient specific negative contour 674 that matches and is a negative of a positive contour of a distal end 40 of a patient's femur 42 (see FIG. 21).

The cutting block 652 includes an anterior flange 654 and a keel 656 extending away from the anterior flange 654. The keel 656 includes a distal segment 658 extending from the anterior flange 654 to a posterior end 660. The keel 656 also includes a posterior segment 662 extending from the posterior end 660 of the distal segment 658. The cutting block 562 also includes a pin guide 680 that extends from an opening 682 formed in the outer surface 670 of the distal segment 658 to an opening 684 (see FIG. 17) in the bone-facing surface 672 of the distal segment 658. Another pin guide 690 extends from an opening 692 formed in the outer surface 670 of the anterior flange 654 to an opening 694 (see FIG. 16) in the bone-facing surface 672 of the anterior flange 654. The pin guides 680, 690 are configured to receive bone fixation pins to retain the cutting block 652 on the distal end 40 of the patient's femur 42.

The anterior flange 654 includes a plurality of flange ribs 700 that are coupled at each end 702 by beams 704. Each rib 700 includes a pair of planar surfaces 706, and each beam 704 includes a planar surface 708. The planar surfaces 706, 708 extend from the outer surface 670 to the bone-facing surface 672. A plurality of slots 710 are defined between their planar surfaces 706 of adjacent ribs 700 and the planar surface 708 of the beam 704 connecting the adjacent ribs 700.

A plurality of medial and lateral ribs 720 extend from the keel 656 to cantilevered ends 722. Each rib 720 includes a pair of planar surfaces 724 extending from the outer surface 670 to the bone-facing surface 672. A plurality of medial and lateral slots 726 are defined by the planar surfaces 724 of adjacent ribs 720 and a planar surface 728 of the keel 656 that extends between the outer surface 670 and the bone-facing surface 672. The slots 726 include open ends 730 positioned between the cantilevered ends 722 of the ribs 720. As described in greater detail below, the slots 710 cooperate with the slots 726 to define a posterior chamfer cutting guide 776, a distal cutting guide 784, a posterior cutting guide 794, an anterior chamfer cutting guide 814, and an anterior cutting guide 842 of the cutting block 652.

Figure 18:
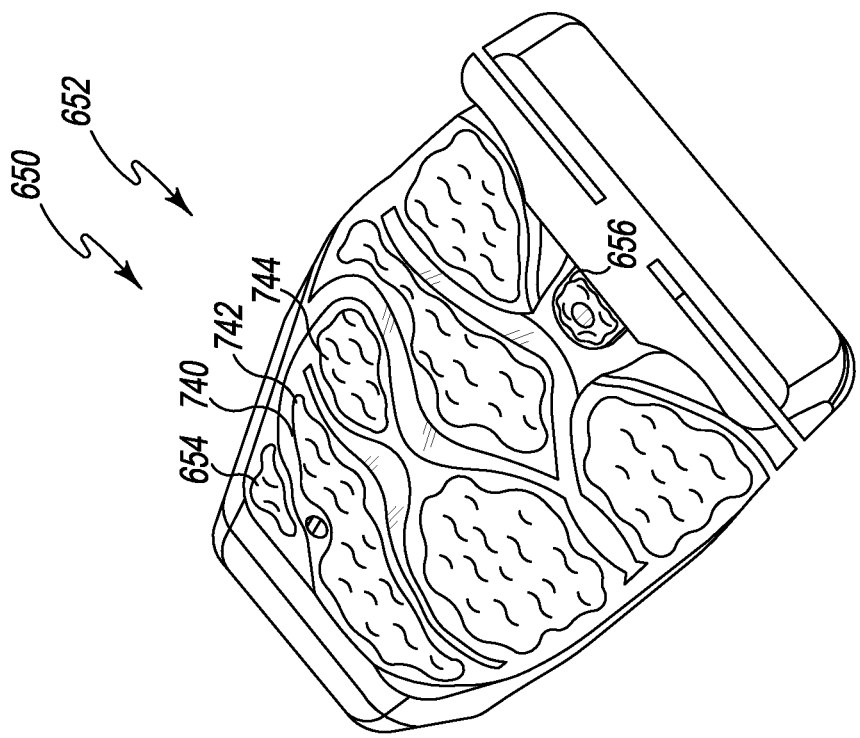
FIG. 18 is another rear perspective view of the instrument shown in FIG. 15.
Figure 17:
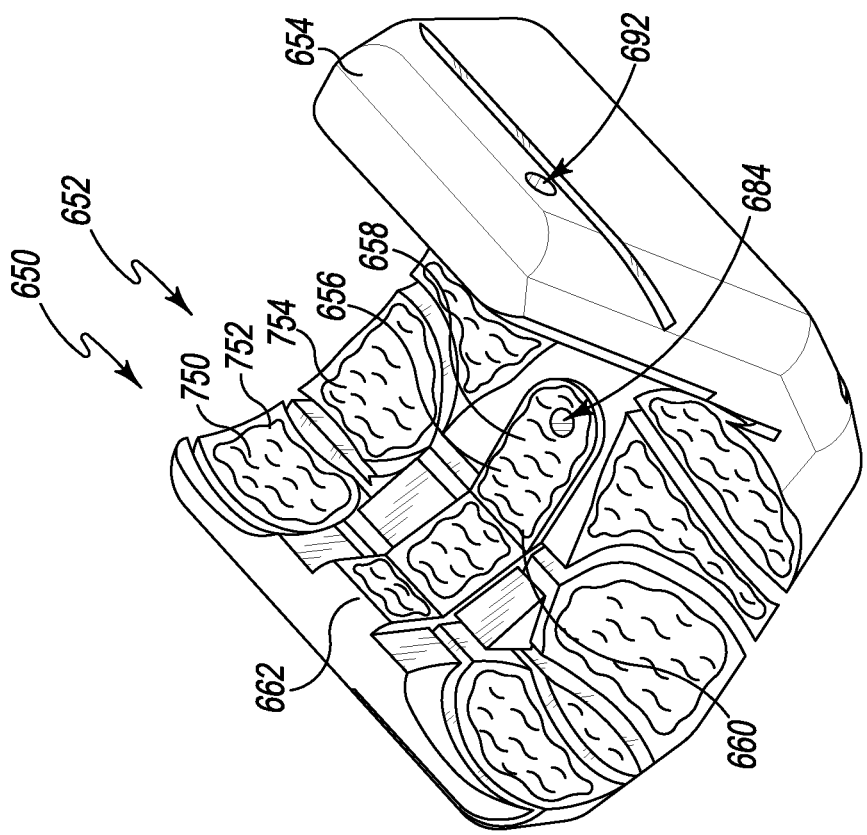
FIG. 17 is a rear perspective view of the instrument shown in FIG. 15.

Referring now to FIGS. 17-18, the negative contour 674 is formed by negative contours 740 defined in the flange ribs 700 and beams 704 and negative contours 750 defined in the medial and lateral ribs 720. The contour 740 has a unique set of ridges 742 and depressions 744 that are shaped to engage a corresponding unique set of depressions 106 and ridges 108 of an anterior surface 110 of the patient's femur 42 (see FIG. 22). The contour 750 also has a unique set of ridges 752 and depressions 754 that are shaped to engage a corresponding unique set of depressions 146 and ridges 148 of the condyles 150 of the patient's femur 42 and the depressions 126 and ridges 128 of the posterior surface 130 of the patient's femur 42. In that way, the cutting block 652 may be positioned in a unique, pre-planned location on the patient's femur 42.

Referring now to FIG. 19, a medial side 760 of the cutting block 652 is illustrated to show the various medial slots 726 of the cutting block 652. It should be noted that a lateral side of the cutting block 652 includes the same slots described herein with respect to the medial side 760. For example, when a posterior cutting slot is referenced, it should be appreciated that the lateral side of the cutting block 652 also includes a posterior cutting slot that corresponds with the posterior cutting slot on the medial side 760 of the cutting block 652.

The cutting block 652 includes a rib 770 and a rib 772 that define a slot 774 between their planar surfaces 724. The slot 774 defines a portion of a medial side of the open posterior chamfer cutting guide 776. The rib 772 and another rib 780 define a slot 782 between their planar surfaces 724, which defines an open portion of a medial side of the distal cutting guide 784.

The rib 780 and another rib 790 of the cutting block 652 define another slot 792 between their planar surfaces 724, which defines a medial side of the open posterior cutting guide 794. The posterior cutting guide 794 is configured to receive a cutting tool and defines a posterior resection guide plane 796 extending through the patient's femur 42.

The rib 790 and another rib 800 define a slot 802 between their planar surfaces 724. The slot 802 is aligned with the slot 774 to define the medial side of the posterior chamfer cutting guide 776. As described above, the cutting block 652 includes another pair of slots on its lateral side that defines the lateral side of the posterior chamfer cutting guide 776. The posterior chamfer cutting guide 776 is configured to receive a cutting tool and defines a posterior chamfer resection guide plane 806 extending through the distal end 40 of the patient's femur 42.

The cutting block 652 includes another rib 810, which cooperates with the rib 800 to define a slot 812 between their planar surfaces 724. The slot 812 defines an open portion of a medial side of an anterior chamfer cutting guide 814.

Referring now to FIG. 20, the rib 810 and ribs 820, 822, 824 cooperate to define a slot 830 between their planar surfaces 724 and 708. The slot 830 is aligned with the slot 782 to define a captured end of the distal cutting guide 784. The distal cutting guide 784 is configured to receive a cutting tool and defines a distal resection guide plane 832 extending through the distal end 40 of the patient's femur 42.

The ribs 810, 820, 822, and 824 also cooperate to define a slot 840 between their planar surfaces 724 and 708. The slot 840 defines a captured anterior cutting guide 842 that is configured to receive a cutting tool and defines an anterior resection guide plane 844 extending through the patient's femur 42.

The rib 824 and another rib 850 define a slot 852 between their planar surfaces 708. The slot 852 is aligned with the slot 812 to define a captured portion of the anterior chamfer cutting guide 814. The anterior chamfer cutting guide 814 is configured to receive a cutting tool and defines an anterior chamfer resection guide plane 856 extending through the distal end 40 of the patient's femur 42.

Figure 22:
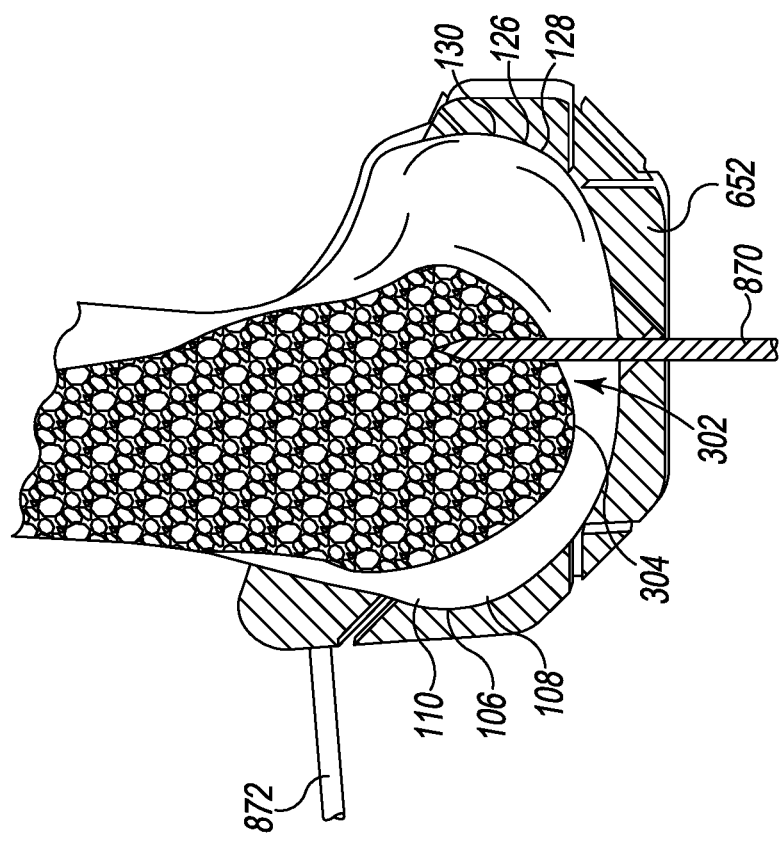
FIG. 22 is a cross-sectional view of the instrument positioned on the distal end of the femur taken along line 22-22 in FIG. 21.
Figure 21:
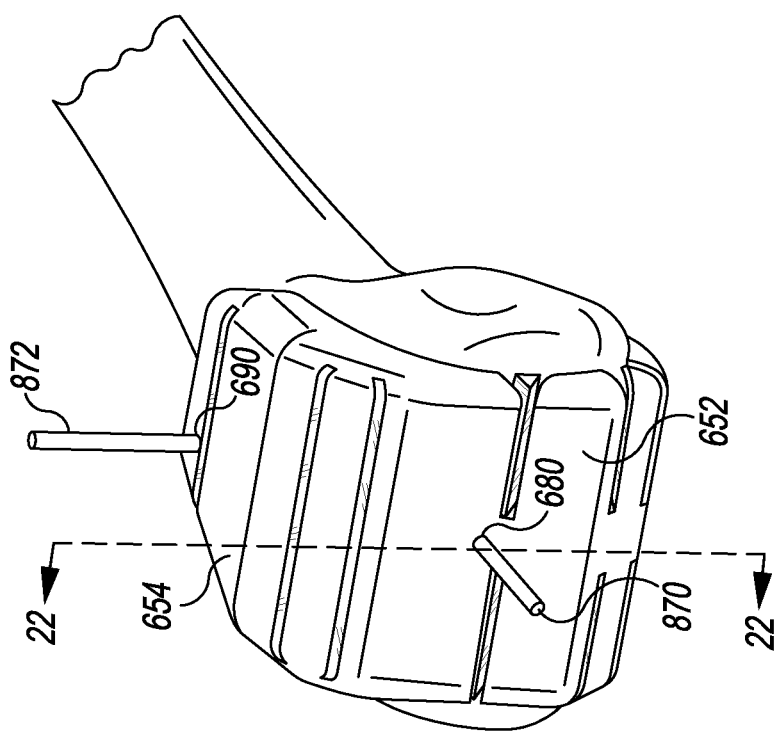
FIG. 21 is a front perspective view of the instrument shown in FIG. 15 positioned on a distal end of a femur.

Referring now to FIG. 21, the pin guide 680 is configured to receive a fixation pin 870 that secures the cutting block 652 to the distal end 40 of the patient's femur 42. The pin 870 is positioned in the patient's intercondylar notch 302, as illustrated in FIG. 22, and is secured to the surface 304 that defines the intercondylar notch 302. The other pin guide 690 is configured to receive a pin 872 that secures the anterior flange 654 to the anterior surface 110 of the patient's femur 42. Because the surgeon can resect around the pins 870, 872, the pins 870, 872 can remain secured to the bone during the surgical procedure. In some embodiments, the surgeon may remove the pin 870 when making some of the cuts so that the surgeon does not have to resection around the pin 870. In such an embodiment, the pin 872 in cooperation with the bone-facing surface 672 holds the cutting block 652 in place on the patient's femur 42.

In each of the embodiments described above, the surgeon may make the anterior, posterior, posterior chamfer, anterior chamfer, and distal resections with a single cutting block (e.g., cutting blocks 12, 352, 652). The cutting block may be attached to the patient's femur in the unique, preplanned location before the first resection is made and may remain in place until the last resection is made, even as bone material is removed by the other resections. It should be appreciated that the cutting blocks may have other configurations to achieve a similar outcome. For example, although the keel is shown positioned at the mid-line in the block 352, in other embodiments the keel may be formed along the medial or lateral side of the block. Additionally, although each of the blocks is shown as a single, monolithic component, it should be appreciated that in other embodiments the blocks may be formed from multiple components that are later assembled. In such embodiments, other materials such as, for example, polyethylene may be used to form part of the components.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It should be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. An orthopaedic surgical instrument comprising:
a customized patient-specific 5-in-1 cutting block, comprising:
an anterior flange including a bone-facing surface having a customized patient-specific negative contour configured to receive a portion of a corresponding positive contour of a patient's femur,
a keel including a distal segment extending from the anterior flange to a posterior end and a posterior segment extending proximally from the posterior end of the distal segment, and
a plurality of ribs extending medially and laterally from the distal segment, and the proximal segment of the keel, each rib including a first end coupled to the keel, a cantilevered second end, and a bone-facing surface extending from the first end to the second end of each rib,
wherein each bone-facing surface of each rib has a customized patient-specific negative contour configured to receive a portion of a corresponding positive contour of the patient's femoral condyle,
wherein the plurality of ribs cooperate to define a plurality of cutting guides, each cutting guide including a slot having an open outer end defined between corresponding cantilevered second ends of adjacent ribs, and wherein a plurality of captured cutting guides extend through the anterior flange.

2. The orthopaedic surgical instrument of claim 1, wherein the keel includes a customized patient-specific negative contour configured to receive a portion of a corresponding positive contour of a surface defining the patient's intercondylar notch.

3. The orthopaedic surgical instrument of claim 1, wherein the cutting guides include a first chamfer cutting guide and a second chamfer cutting guide.

4. The orthopaedic surgical instrument of claim 3, wherein:
 the first chamfer cutting guide includes a first slot aligned with a second slot, and
 the second chamfer cutting guide includes a third slot aligned with a fourth slot.

5. The orthopaedic surgical instrument of claim 1, wherein the cutting guides include a distal cutting guide, an anterior cutting guide, and a posterior cutting guide.

\* \* \* \* \*